(12) United States Patent
Nagai et al.

(10) Patent No.: US 7,193,119 B2
(45) Date of Patent: Mar. 20, 2007

(54) PROCESS FOR PRODUCING FLUORINATED ALKYL ETHER

(75) Inventors: Masazumi Nagai, Ichihara (JP); Hidekazu Okamoto, Yokohama (JP); Kazuya Oharu, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/348,490

(22) Filed: Feb. 7, 2006

(65) Prior Publication Data
US 2006/0128915 A1    Jun. 15, 2006

Related U.S. Application Data

(63) Continuation of application No. PCT/JP04/11338, filed on Aug. 6, 2004.

(30) Foreign Application Priority Data
Aug. 11, 2003   (JP)   ............ 2003-291456

(51) Int. Cl.
*C07C 41/00*   (2006.01)
(52) U.S. Cl. .............. 568/683; 568/413; 568/681; 526/247; 528/401
(58) Field of Classification Search ............ 568/683, 568/681, 413; 528/401; 526/247
See application file for complete search history.

(56) References Cited

U.S. PATENT DOCUMENTS 3,557,294 A    1/1971    Dear et al.
4,960,951 A * 10/1990   Nappa et al. ............... 568/615
5,750,797 A *  5/1998   Vitcak et al. ............... 568/683
6,046,368 A *  4/2000   Lamanna et al. ........... 568/683

FOREIGN PATENT DOCUMENTS

| EP | 344935 A2 * | 12/1989 |
| EP | 1655278 A1 * | 5/2006 |
| JP | 2-62840 | 3/1990 |
| JP | 9-263559 | 10/1997 |

OTHER PUBLICATIONS

A. V. Fokin, et al., "Reaction of Polyfluorinated Alcohols With Fluoroolefins", Database CA [Online], Database Accession No. 1978:22065, XP-002403493, 1997, 1 page.

* cited by examiner

*Primary Examiner*—David W. Wu
*Assistant Examiner*—Henry S. Hu
(74) *Attorney, Agent, or Firm*—Oblon, Spivak, McClelland, Maier & Neustadt, P.C.

(57) ABSTRACT

To provide a process for producing a fluorinated alkyl ether, whereby a sufficient reaction rate can be attained even under mild reaction conditions, and a post-process such as distillation after the reaction can be efficiently carried out.

A process for producing a fluorinated alkyl ether, which comprises introducing an aprotic polar solvent, a fluorinated ether, a catalyst, a fluorinated alkyl alcohol and a fluorinated olefin into a reactor, and then, reacting the fluorinated alkyl alcohol with the fluorinated olefin, characterized in that the ratio of the two components of the aprotic polar solvent and the fluorinated ether introduced into the reactor is the aprotic polar solvent/the fluorinated ether=5/95 to 80/20 by mass ratio.

7 Claims, No Drawings

PROCESS FOR PRODUCING FLUORINATED ALKYL ETHER

TECHNICAL FIELD

The present invention relates to a process for producing a fluorinated alkyl ether.

BACKGROUND ART

Among fluorinated alkyl ethers, one containing no halogen other than fluorine is considered not to destroy the ozone layer and thus is a compound expected to be a substitute for a chlorofluorocarbon or a hydrochlorofluorocarbon which has been used as a CFC.

As a method for preparing a fluorinated alkyl ether, a method is known wherein a fluorinated alkyl alcohol and a fluorinated olefin are reacted in the presence of an alkali metal or an alkali metal hydroxide (Patent Document 1). However, such a method requires reaction conditions such as high temperature and high pressure, and yet, the reaction rate is low.

Under the circumstances, as a method to improve the above method, a method for synthesizing a fluorinated alkyl ether by reacting a fluorinated alkyl alcohol and a fluorinated olefin in an aprotic polar solvent, has been reported (Patent Document 2). However, even when this method is employed, there has been a problem such that in order to obtain a sufficient reaction rate, a high reaction pressure is required, and since a large amount of the aprotic polar solvent is required, a post-process such as distillation is required.

Patent Document 1: U.S. Pat. No. 3,557,294 (Examples)
Patent Document 2: JP-A-9-263559 (claims, Examples)

DISCLOSURE OF THE INVENTION

OBJECT TO BE ACCOMPLISHED BY THE INVENTION

It is an object of the present invention to provide a process for producing a fluorinated alkyl ether, whereby a sufficient reaction rate can be obtained even under mild reaction conditions, and a post-process such as distillation after the reaction can be efficiently carried out.

MEANS TO ACCOMPLISH THE OBJECT

The present inventors have studied in detail the change with time of the reaction rate in a batch reaction and have surprisingly found that the reaction rate becomes sharply high at the final stage of the reaction i.e. from a stage where the fluorinated alkyl ether as the desired product has been formed in a concentration of at least a certain level, and that the reaction rate immediately before the termination of the reaction is remarkably high as compared with the initial stage of the reaction. This phenomenon is considered to be attributable to an increase in the solubility of the fluorinated olefin due to an increase of the content of the fluorinated alkyl ether. The present inventors have conducted a further study on the above finding and have found that the above-mentioned acceleration of the reaction rate is not limited to the fluorinated alkyl ether but also when a fluorinated ether is permitted to be present in the reaction system at a concentration of at least a certain level. Namely, it has been found that the reaction rate can be improved by permitting two components of the fluorinated ether and the aprotic polar solvent in a prescribed ratio in the reactor. The present invention has been accomplished on the basis of these discoveries.

Thus, the present invention provides a process for producing a fluorinated alkyl ether, which comprises introducing an aprotic polar solvent, a fluorinated ether, a catalyst, a fluorinated alkyl alcohol and a fluorinated olefin into a reactor, and then, reacting the fluorinated alkyl alcohol with the fluorinated olefin, characterized in that the ratio of the two components of the aprotic polar solvent and the fluorinated ether introduced into the reactor is the aprotic polar solvent/the fluorinated ether=5/95 to 80/20 by mass ratio.

EFFECTS OF THE INVENTION

According to the present invention, a fluorinated alkyl ether can be produced at a high reaction rate and in high purity under mild reaction conditions, and the following process such as distillation after the reaction can also be carried out efficiently.

BEST MODE FOR CARRYING OUT THE INVENTION

Now, the process of the present invention will be described in detail.

In the present invention, the ratio of the two components of the aprotic polar solvent and the fluorinated ether introduced into the reactor is adjusted to be the aprotic polar solvent/the fluorinated ether=5/95 to 80/20, preferably 10/90 to 70/30, particularly preferably 10/90 to 50/50, by mass ratio. When the ratio of these two components is adjusted to be within the above range, the reaction rate can be improved.

In the present invention, as the fluorinated ether to be introduced into the reactor, it is preferred to employ the fluorinated alkyl ether as the desired product. When the fluorinated alkyl ether as the desired product is employed, there is a merit such that after completion of the reaction, such a product is not required to be separated by distillation. Otherwise, as the above fluorinated ether, any fluorinated ether may be used without any particular restriction, so long as it is a fluorinated ether readily separable by distillation from the fluorinated alkyl ether as the desired product after completion of the reaction.

The fluorinated alkyl alcohol as the raw material to be used in the present invention may be any fluorinated alkyl alcohol so long as it is a compound having some of hydrogen atoms of a saturated hydrocarbon alcohol other than a hydroxyl group substituted by fluorine atoms, and it may be an alcohol having a fluorinated cycloalkyl group. However, it is preferably a compound represented by the Formula 1, if the production in an industrial scale of the fluorinated alkyl ether as the product and the effects in the application fields, are taken into consideration.

RR'CHOH   Formula 1

Here, in the Formula 1, R is $-C_aH_bF_dX_e$ (X is a halogen atom other than a fluorine atom, each of a and d is an integer of at least 1, each of b and e is an integer of at least 0, and $b+d+e=2a+1$), R' is a hydrogen atom or $-C_fH_gF_hX_i$ (X is a halogen atom other than a fluorine atom, each of f and h is an integer of at least 1, each of g and i is an integer of at least 0, and $g+h+i=2f+1$).

In the Formula 1, a is preferably an integer of from 1 to 10, particularly preferably an integer of from 1 to 4, from the viewpoint of availability, and e is preferably 0.

Further, likewise, f is preferably an integer of from 1 to 10, particularly preferably an integer of from 1 to 4, and i is preferably 0.

Among the compounds represented by the Formula 1, a preferred fluorinated alkyl alcohol may specifically be e.g. $CF_3CH_2OH$, $CF_3CF_2CH_2OH$, $CF_3(CF_2)_2CH_2OH$, $CF_3(CF_2)_3CH_2OH$, $CF_3(CF_2)_4CH_2OH$, $CF_3(CF_2)_5CH_2OH$, $CF_3(CF_2)_6CH_2OH$, $CHF_2CF_2CH_2OH$, $CHF_2(CF_2)_3CH_2OH$, $CHF_2(CF_2)_5CH_2OH$, $CF_3CHFCF_2CH_2OH$, $CHF_2CF(CF_3)CH_2OH$ or $CClF_2CF_2CH_2OH$.

Among them, a particularly preferred fluorinated alkyl alcohol may be $CF_3CH_2OH$ (2,2,2-trifluoroethanol, hereinafter referred to as TFEO).

Further, as the fluorinated olefin as another raw material in the present invention, a compound represented by the Formula 2 is preferred:

$$CF_2=CYZ \qquad \text{Formula 2}$$

In the Formula 2, each of Y and Z which are independent of each other, is a hydrogen atom, a fluorine atom, a chlorine atom, a bromine atom or a trifluoromethyl group.

Among compounds represented by the Formula 2, those which are preferably employed, may be $CF_2=CF_2$, $CF_2=CHF$, $CF_2=CH_2$, $CF_2=CFCF_3$. Among them, a perfluoroolefin is preferred, and most preferred is $CF_2=CF_2$ (tetrafluoroethylene, hereinafter referred to also as TFE).

As the fluorinated alkyl ether obtainable by the process of the present invention, a compound represented by the Formula 3 (wherein R and R' are the same as in the Formula 1, and Y and Z are the same as in the Formula 2) may be mentioned:

$$RR'CHOCF_2CHYZ \qquad \text{Formula 3}$$

The compound represented by the Formula 3 may specifically be $CF_3CH_2OCF_2CF_2H$, $CF_3CF_2CH_2OCF_2CF_2H$, $CF_3(CF_2)_2CH_2OCF_2CF_2H$, $CHF_2CF_2CH_2OCF_2CF_2H$, $CF_2(CF_2)_3CH_2OCF_2CF_2H$, $CHF_2(CF_2)_5CH_2OCF_2CF_2H$, $CF_3CHFCF_2CH_2OCF_2CF_2H$, $CHF_2CF(CF_3)CH_2OCF_2CF_2H$, $CClF_2CF_2CH_2OCF_2CF_2H$, $CF_3CH_2OCF_2CFHCF_3$, $CF_3CF_2CH_2OCF_2CFHCF_3$, $CF_3(CF_2)_2CH_2OCF_2CFHCF_3$, $CHF_2CF_2CH_2OCF_3CFHCF_3$, $CHF_2(CF_2)_3CH_2OCF_2CFHCF_3$, $CHF_2(CF_2)_5CH_2OCF_2CFHCF_3$, $CF_3CHFCF_2CH_2OCF_2CFHCF_3$, $CHF_2CF(CF_3)CH_2OCF_2CFHCF_3$ or $CClF_2CF_2CH_2OCF_2CFHCF_3$.

From the viewpoint of efficiency in separation of the desired product by distillation purification, the present invention is preferably applied to a case of producing a fluorinated alkyl ether by a reaction of the fluorinated alcohol of the Formula 1 with the fluorinated olefin of the Formula 2. For example, it is preferably employed in a case where 1,1,2,2-tetrafluoro-1-(2,2,2-trifluoroethoxy)ethane is produced as the fluorinated alkyl ether by using TFEO as the fluorinated alkyl alcohol and TFE as the fluorinated olefin.

Further, the present invention may be applied to a process for producing 1,1,2,3,3,3-hexafluoro-1-(2,2,3,3-tetrafluoropropoxy)propane by using 2,2,3,3-tetrafluoro-1-propanol and hexafluoropropene, or a process for producing 1,1,2,3,3,3-hexafluoro-1-(2,2,2-trifluoroethoxy)propane by using 2,2,2-trifluoroethanol and hexafluoropropene.

Further, as the aprotic polar solvent in the present invention, a compound, such as diethyl ether or a glyme, a cyclic ether such as dioxane or tetrahydrofuran, or a nitrile compound such as acetonitrile or propionitrile, may be used. Among them, it is preferred to employ a compound represented by the Formula 4, since the reaction rate can thereby be remarkably improved:

$$R^1O(R^2O)_mR^3 \qquad \text{Formula 4}$$

In the Formula 4, each of $R^1$ and $R^3$ which are independent of each other, is a hydrogen atom or a $C_{1-4}$ alkyl group, $R^2$ is a $C_{1-4}$ alkylene group, and m is an integer of at least 0.

Among compounds represented by the Formula 4, a compound represented by $R^4-O-(CH_2CH_2O)_n-R^6$ (wherein each of $R^4$ and $R^6$ which are independent of each other, is a $C_{1-4}$ alkyl group, and n is an integer of from 1 to 4) is preferred. Specifically, a glyme such as glyme or tetraglyme is preferred. Particularly, tetraglyme is most preferably employed, since the reaction rate is thereby particularly high.

Further, the total of contents of the aprotic polar solvent and the fluorinated ether to be present at the initiation of the reaction, is not particularly limited. However, it is usually preferably from 1 to 10,000 parts by mass per 1 part by mass of the fluorinated alkyl alcohol, particularly preferably from 50 to 2,000 parts by mass, in consideration with the reaction rate, and the productivity.

The catalyst to be used in the present invention is not particularly limited so long as it is a basic compound. From the viewpoint of the general applicability and the basicity, it is preferred to employ an alkali metal alkoxide or an alkali metal hydroxide.

As such an alkali metal alkoxide, a commercial product may be used as it is, but one obtained by reacting an alkali metal, an alkali metal hydride or an alkali metal amide with an alcohol, may be used. The alcohol to be used in this reaction is not particularly limited, but it is preferred to employ a fluorinated alkyl alcohol to be used as the raw material in the present invention. Further, in the above reaction, the alkali metal may, for example, be Na, K or Cs; the alkali metal hydride may, for example, be NaH or KH; and the alkali metal amide may, for example, be $NaNH_2$ or $KNH_2$.

Further, as the alkali metal hydroxide, NaOH or KOH is particularly preferably employed from the viewpoint of the handling efficiency or availability. Such an alkali metal hydroxide has a merit that it can be used in the form of an aqueous solution.

In the present invention, the content of the catalyst is not particularly limited, but it is usually preferably from 0.01 to 10 mol equivalent to the fluorinated alkyl alcohol as the starting material. If the content of the catalyst is too small, the reaction rate tends to be slow, and if it is too large, a by-product tends to increase. Accordingly, the content of the catalyst is particularly preferably from 0.1 to 5 mol equivalent.

In the present invention, the reaction pressure is preferably high with a view of increasing the reaction rate. However, if the pressure for the reaction is too high, there will be a problem such that a by-product may be formed by a polymerization reaction of the fluorinated olefin, or a disproportionation reaction occur. Therefore, the reaction pressure is preferably from atmospheric pressure to 2 MPa (gauge pressure). Further, according to the present invention, even under a low pressure, the reaction proceeds at a reaction rate faster than the conventional rate. Accordingly, the reaction pressure is usually preferably set to be from 0.01 to 1 MPa (gauge pressure).

In the present invention, the reaction temperature may take a various level depending upon the types, etc. of the fluorinated alkyl alcohol, the fluorinated olefin, the catalyst and the aprotic polar solvent to be used. However, it is usually within a range of from 0 to 120° C., particularly preferably within a range of from 30 to 80° C.

In the present invention, if a relatively high reaction pressure or reaction temperature is adopted as a reaction

Example 5

Comparative Example

The reaction was carried out in the same manner as in Examples 1 to 4 except that 250 g of tetraglyme was used instead of using 250 g of a mixture of tetraglyme and HFE347 pc-f. The results are shown in Table 1.

TABLE 1

| Example | Tetraglyme concentration (mass %) | TFEO (mass %) | HFE347pc-f (mass %) | Tetraglyme (mass %) | Others (mass %) | Reaction time (hrs) | Yield (%) |
|---|---|---|---|---|---|---|---|
| 1 | 5 | 0 | 95.0 | 4.3 | 0.7 | 1.15 | 98 |
| 2 | 10 | 0 | 90.9 | 8.6 | 0.5 | 0.68 | 99 |
| 3 | 25 | 0 | 78.0 | 21.4 | 0.5 | 0.33 | 98 |
| 4 | 50 | 0 | 56.7 | 43.0 | 0.3 | 0.75 | 97 |
| 5 | 100 | 0 | 13.7 | 85.9 | 0.3 | 1.25 | 98 | condition, it is likely that the fluorinated olefin undergoes a polymerization reaction. In such a case, it is preferred to add a polymerization inhibitor to suppress such a polymerization reaction. The polymerization inhibitor is not particularly limited, and limonene, pinene, cymene or terpinene may, for example, be mentioned.

The process of the present invention is suitable for a batch reaction, but the method for introducing the raw material, the catalyst and the solvent is not particularly limited, and it is possible to employ a method wherein the fluorinated alkyl alcohol, the catalyst and the aprotic polar solvent are introduced all at once into a reactor, and then, the fluorinated olefin is continuously introduced, or a method wherein the catalyst and the aprotic polar solvent are introduced all at once, and then, the fluorinated alkyl alcohol and the fluorinated olefin are continuously supplied in equimolar amounts.

EXAMPLES

Now, the present invention will be described with reference to Examples.

Examples 1 to 4

20.0 g of TFEO as a raw material, 20 g of a 48 mass % potassium hydroxide aqueous solution as a catalyst and 250 g of a mixed liquid of tetraglyme and 1,1,2,2-tetrafluoro-1-(2,2,2-trifluroethoxy)ethane (hereinafter referred to as HFE347 pc-f) (the mixed liquid was prepared in four patterns i.e. the tetraglyme concentration being 5 mass % (Example 1), 10 mass % (Example 2), 25 mass % (Example 3) and 50 mass % (Example 4) based on the total amount of both) were charged into a 500 mL autoclave, and the autoclave was closed. The autoclave was cooled with liquid nitrogen, followed by deaeration. The temperature was raised to 50° C., and then stirring was initiated at 300 rpm. Then, TFE was continuously supplied so that the reaction pressure (gauge pressure) became 0.2 MPa, and the reaction was carried out. The reaction was terminated when a change in the amount of TFE used, was no longer observed, and after cooling, the obtained reaction solution was analyzed by gas chromatograph, and HFE347 pc-f and TFEO were quantified. The results are shown in Table 1.

In Example 3 wherein the tetraglyme concentration at the time of charging was 25 mass %, the reaction rate was highest, and the reaction rate was about 3.5 times as compared with the case of tetraglyme only (Example 5).

Example 6

The reaction was carried out in the same manner as in Example 2 except that the amount of the mixed liquid of tetraglyme and HFE347 pc-f was changed to 258 g. The reaction time was 0.6 hour, and no TFEO was present in the obtained reaction solution. The yield was 98%.

Example 7

The test of the reaction was carried out in the same manner as in Example 6 except that diglyme was used instead of tetraglyme. The reaction time was 4.8 hours, and no TFEO was present in the obtained reaction solution. The yield was 98%.

INDUSTRIAL APPLICABILITY

The fluorinated alkyl ether obtainable by the process of the present invention is useful as a cleaning agent or cosolvent for flux cleaning, precision cleaning, draining/drying, etc.

The entire disclosure of Japanese Patent Application No. 2003-291456 filed on Aug. 11, 2003 including specification, claims and summary is incorporated herein by reference in its entirety.

What is claimed is:

1. A process for producing a fluorinated alkyl ether, which comprises introducing an aprotic polar solvent, a fluorinated ether, a catalyst, a fluorinated alkyl alcohol and a fluorinated olefin into a reactor, and then, reacting the fluorinated alkyl alcohol with the fluorinated olefin, characterized in that the ratio of the two components of the aprotic polar solvent and the fluorinated ether introduced into the reactor is the aprotic polar solvent/the fluorinated ether=5/95 to 80/20 by mass ratio.

2. The process for producing a fluorinated alkyl ether according to claim 1, wherein the fluorinated alkyl alcohol is a compound represented by the Formula 1, the fluorinated olefin is a compound represented by the Formula 2, and a fluorinated alkyl ether represented by the Formula 3 is produced:

RR'CHOH        Formula 1

$CF_2$=CYZ        Formula 2

RR'CHOCF$_2$CHYZ        Formula 3 provided that in the Formula 1 to 3, R is —$C_aH_bF_dX_e$ (X is a halogen atom other than a fluorine atom, each of a and d is an integer of at least 1, each of b and e is an integer of at least 0, and b+d+e=2a+1), R' is a hydrogen atom or —$C_fH_gF_hX_i$ (X is a halogen atom other than a fluorine atom, each of f and h is an integer of at least 1, each of g and i is an integer of at least 0, and g+h+i=2f+1), and each of Y and Z which are independent of each other, is a hydrogen atom, a fluorine atom, a chlorine atom, a bromine atom or a trifluoromethyl group.

3. The process for producing a fluorinated alkyl ether according to claim 2, wherein the fluorinated ether introduced into the reactor is the fluorinated alkyl ether represented by the Formula 3, as the desired product.

4. The process for producing a fluorinated alkyl ether according to claim 1, wherein the aprotic polar solvent is a compound represented by the Formula 4:

$R^1O(R^2O)_mR^3$        Formula 4 provided that in the Formula 4, each of $R^1$ and $R^3$ which are independent of each other, is a hydrogen atom or a $C_{1-4}$ alkyl group, $R^2$ is a $C_{1-4}$ alkylene group, and m is an integer of at least 0.

5. The process for producing a fluorinated alkyl ether according to claim 4, wherein the compound represented by the Formula 4 is diglyme, triglyme or tetraglyme.

6. The process for producing a fluorinated alkyl ether according to claim 2, wherein the fluorinated alkyl alcohol represented by the Formula 1 is $CF_3CH_2OH$, the fluorinated olefin represented by the Formula 2 is $CF_2$=$CF_2$, and $CF_3CH_2OCF_2CHF_2$ is produced as the fluorinated alkyl ether represented by the Formula 3.

7. The process for producing a fluorinated alkyl ether according to claim 1, wherein the reaction is carried out under a pressure (gauge pressure) of at most 1 MPa.

* * * * *